US 6,642,414 B2

(12) United States Patent
Mitsumoto et al.

(10) Patent No.: US 6,642,414 B2
(45) Date of Patent: Nov. 4, 2003

(54) METHOD FOR PRODUCTION OF (METH) ACRYLIC ACID

(75) Inventors: Tetsuji Mitsumoto, Himeji (JP); Yukihiro Matsumoto, Kobe (JP); Sei Nakahara, Himeji (JP); Tatsuaki Yoshimura, Ibo-gun (JP)

(73) Assignee: Nippon Shokubai Co., Ltd. (JP)

( * ) Notice: Subject to any disclaimer, the term of this patent is extended or adjusted under 35 U.S.C. 154(b) by 100 days.

(21) Appl. No.: 09/772,458

(22) Filed: Jan. 30, 2001

(65) Prior Publication Data

US 2001/0016668 A1 Aug. 23, 2001

(30) Foreign Application Priority Data

Feb. 3, 2000 (JP) ........................................ 2000-026149

(51) Int. Cl.$^7$ ........................... C07C 51/42; C07C 57/02
(52) U.S. Cl. ........................................ 562/600; 562/598
(58) Field of Search ................................ 562/600, 598

(56) References Cited

U.S. PATENT DOCUMENTS

| 3,926,744 A | * 12/1975 | Noll et al. ..................... 203/55 |
| 5,315,037 A | 5/1994 | Sakamoto et al. ........... 562/545 |
| 5,785,821 A | 7/1998 | Sakamoto et al. ............. 203/57 |
| 6,069,271 A | 5/2000 | Tanimoto et al. ............ 562/545 |

FOREIGN PATENT DOCUMENTS

| EP | 0887334 | 12/1998 | ......... C07C/51/487 |
| GB | 2146636 | 4/1985 | ............ C07C/51/48 |
| JP | A 61218556 | 9/1986 | ............ C07C/57/07 |

* cited by examiner

*Primary Examiner*—Alan L. Rotman
*Assistant Examiner*—Taylor V. Oh
(74) *Attorney, Agent, or Firm*—Mathews, Collins, Shepherd & McKay, P.A.

(57) ABSTRACT

A method for producing (meth)acrylic acid of high purity by repressing formation of a polymer possibly generated during the course of production is disclosed. The production is accomplished by returning the waste liquid generated at the step of the addition of aldehyde treating agents (d) to the step of the absorption (b) and/or the step of separation (c).

20 Claims, No Drawings

METHOD FOR PRODUCTION OF (METH) ACRYLIC ACID

BACKGROUND OF THE INVENTION

1. Field of the Invention

This invention relates to a method for the production of (meth)acrylic acid.

2. Description of the Related Art

Heretofore, (meth)acrylic acid has been produced by subjecting propylene and/or acrolein or isobutylene and/or methacrolein to catalytic gas phase oxidation. Since the product of this reaction contains by-products such as (meth) acrolein, acetic acid, and formaldehyde besides the (meth) acrylic acid, it is necessary for the purpose of producing the (meth)acrylic acid in high purity to separate and remove such by-products by the use of distillation or the like.

JP-A-61-218,556, for example, discloses a method which, in a process of removing a light boiling substance by the operation of distillation or stripping from the aqueous acrylic acid solution resulting from the operation of cooling condensing an acrylic acid-containing gas and then separating and refining acrylic acid from the resultant aqueous acrylic acid solution by treating the aqueous acrylic acid solution sequentially through the step of extraction, the step of solvent separation, the step of light boiling substance separation, the step of heavy boiling substance separation, and the step of effecting refinement by repeated distillation, comprises subjecting the aqueous acrylic acid solution supplied to the step of extraction or the extractant derived in a form containing an extraction solvent and acrylic acid from this step to a treatment for the admixture of an aqueous solution of bisulfites and further admixing a hydrazine compound with the acrylic acid containing solution in at least one step selected from among the steps of solvent separation, of light boiling substance separation, of heavy boiling substance separation, and of effecting refinement by repeated distillation.

The method disclosed in this publication, however, necessitates separation into two layers the product of the admixture of the aqueous bisulfite solution with the acrylic acid containing solution, and consequently complicates the relevant operation.

It also entails the problem of readily generating a polymer at the step of heavy substance separation and the step of effecting refinement by repeated distillation.

It further entails the problem of inducing clogging of the pipe being used in transferring the bottoms as for the purpose of waste disposal at the step of effecting refinement by repeated distillation.

SUMMARY OF THE INVENTION

This invention has been produced in the light of the state of affairs mentioned above and has for an object thereof the provision of a method for repressing the generation of a polymer and permitting production of (meth)acrylic acid of high purity in a high yield.

The object of this invention is achieved by a method for the production of (meth)acrylic acid which comprising (a) a step of obtaining a gaseous reaction product containing (meth)acrylic acid by subjecting at least one member selected from the group consisting of propylene, propane, acrolein, and mixtures thereof (for the case of producing acrylic acid) or at least one member selected from the group consisting of isobutylene, t-butyl alcohol, methyl-t-butyl ether, methacrolein, and mixtures thereof (for the case of producing methacrylic acid) to the reaction of catalytic gas phase oxidation, (b) a step of absorbing the gaseous reaction product by the use of a solvent, (c) a step of separating the solvent, a low boiling impurity, and a high boiling impurity from the (meth)acrylic acid solution absorbed with the solvent mentioned above by extraction and/or distillation and obtaining crude (meth)acrylic acid solution containing aldehydes and the like having boiling points approximating closely to the boiling point of (meth)acrylic acid as impurities, (d) a step of adding an aldehyde treating agent to the crude (meth)acrylic acid mentioned above and subjecting the resultant mixture to vacuum distillation thereby obtaining (meth)acrylic acid of high purity, and (e) a step of returning the waste liquid generated at the step (d) mentioned above to the step (b) and/or the step (c).

This invention is capable of repressing the generation of a polymer and, at the same time, increasing the yield of (meth)acrylic acid of high purity.

In accordance with this invention, the circulation of the waste liquid permits elimination of the otherwise necessary disposal of the waste liquid generated at the step (d) and represses the trouble of clogging of the pipe for discharging the bottoms.

The above and other objects, features and advantages of the present invention will become clear from the following description of the preferred embodiments.

DESCRIPTION OF THE PREFERRED EMBODIMENT(S)

This invention will be specifically described below based on the respective steps (a)–(e) by citing a typical example of the method for the production of acrylic acid.

Step (a)

The step of obtaining a gaseous reaction product containing acrylic acid by subjecting at least one member selected from the group consisting of propylene, acrolein, and a mixture thereof to the reaction of catalytic gas phase oxidation This step is not particularly restricted so long as it is capable of obtaining acrylic acid by the reaction of catalytic gas phase oxidation. For example, the following known method may be adopted.

Propylene and/or acrolein are oxidized by being allowed to contact oxygen or a molecular oxygen-containing gas such as air in the presence of a known catalyst. Generally, the reaction of oxidation is carried out in two stages. The catalyst to be effectively used in the first stage of the reaction is only required to be capable of causing gas phase oxidation of a raw material gas containing propylene and forming mainly acrolein, and the catalyst to be effectively used in the second stage of the reaction to be capable of causing gas phase oxidation of a raw material gas containing acrolein and forming mainly acrylic acid. For example, a complex oxide that contains iron, molybdenum, and bismuth can be cited as the catalyst for the first stage, and a catalyst having vanadium as an essential component as the catalyst for the second stage. The temperature of the oxidation is generally in the range of 250–380° C. (see JP-A-11-130,722).

The gaseous reaction product obtained by this reaction of catalytic gas phase oxidation contains acrylic acid, molecular oxygen-containing gas, and the unreacted raw materials and further contains by-produced water and such impurities as acetic acid, propionic acid, maleic acid, acetone, acrolein, furfural, and formaldehyde.

Step (b)

The step (b) of absorbing the gaseous reaction product mentioned above by the use of a solvent For the purpose of recovering acrolein and/or acrylic acid from the gaseous reaction product obtained at the step (a), the gaseous reaction product is contacted with a solvent. The solvent is not particularly defined but only required to be capable of absorbing and dissolving acrolein and/or acrylic acid. As examples of the solvent usable herein, organic compounds such as diphenyl ether, diphenyl, and a mixture thereof, water and organic substances such as acrylic acid, and acetic acid may be cited. Further, the wastewater that is generated during the step of production of acrylic acid, the waste liquid occurring in a vacuum generating device, and occasionally the cleaning water may be mixed and used as the solvent. The resultant solution containing the produced acrylic acid will be referred to hereinafter as "acrylic acid solution".

The contact of the acrylic acid-containing gaseous reaction product with the solvent may be effected by adopting any of the known methods which are available for establishing the contact of the sort in question. As examples of the method usable herein, crossflow contacts using a bubble-cap tray, a uniflux tray, a sieve tray, a jet tray, a valve tray, a ventury tray, and an arbitrary combination thereof; and counterflow contacts using a turbo grid tray, a dual flow tray, a ripple tray, a kittel tray, a random packing, a structure packing, and an arbitrary combination thereof may be cited.

The acrylic acid solution obtained contains the aforementioned impurities in a small amount besides the acrylic acid. Acetone, acrolein, formaldehyde, etc., when necessary, may be removed by means of stripping or distillation.

To the acrylic acid solution, when necessary, a polymerization inhibitor such as hydroquinone may be added.

Step (c)

The step of separating by distillation the solvent, low boiling impurity, and high boiling impurity from the acrylic acid solution absorbed with the solvent as described above and consequently obtaining crude acrylic acid containing impurities, such as aldehydes, which have boiling points approximating closely to the boiling point of acrylic acid This step embraces an operation of separating the solvent, an operation of separating a low boiling impurity, an operation of separating a high boiling impurity, and an optional operation of recovering acrylic acid as sub-steps. These sub-steps may be sequentially carried out in an arbitrary order. Further, a plurality of such sub-steps of separation may be performed in a sole distillation column.

The term "low boiling impurity" as used herein refers to a compound that exists in the reaction impurities or the solvent for use in the process of production and that exhibits a boiling point lower than the boiling point of acrylic acid. As examples of the low boiling impurity, water and acetic acid may be cited. The term "high boiling impurity" as used herein refers to a compound that exists in the reaction impurity or the solvent for use in the process of production and that exhibits a higher boiling point than the boiling point of acrylic acid. As an example of the high boiling impurity, maleic anhydride may be cited.

Now, this invention will be described below with reference to a process that uses water as a solvent, removes the solvent and the low boiling impurity, and then separates the high boiling impurity by distillation, for example. Of course, this invention is not limited to this example.

Method for Separating Water and Low Boiling Impurity

As examples of the method for separating the water and low boiling impurity, the method of solvent extraction which effects recovery of acrylic acid from the acrylic acid solution by the use of an extraction solvent and the method of azeotropic separation which effects distillation by the use of an azeotropic solvent which forms an azeotropic mixture with water thereby expelling the azeotropic mixture of water with the solvent through the top of the azeotropic distillation column and recovering acrylic acid through the bottom of the column may be cited. From the viewpoint of the convenience of operation, the azeotropic separation method leads all the other conceivable methods of separation.

Now, the azeotropic separation method will be described below.

Azeotropic solvents, which are used in processes for obtaining crude acrylic acid from the aqueous acrylic acid solution by means of azeotropic distillation, are disclosed in numerous patent publications. The method of one-column distillation which effects simultaneous removal of water and acetic acid in one sole distillation column (see JP-A-05-246,491) and the method of two-column distillation which removes water in an azeotropic distillation column and then removes acetic acid in a light boiling separation distillation column (see JP-B-06-15,496) have been described in such patent publications.

As examples of the azeotropic solvent, a solvent containing at least one member selected from the group consisting of heptane, dimethyl cyclohexane, ethyl cyclohexane, toluene, ethyl benzene, chlorobenzene, xylene, and a mixture thereof;

a solvent containing at least one member selected from the group consisting of diethyl ketone, diisopropyl ketone, methylpropyl ketone, methylisobutyl ketone, methyl-t-butyl ketone, n-propyl acetate, n-butyl acetate, ethyl acrylate, methyl methacrylate, ethyl methacrylate, vinyl acrylate, n-propyl acrylate, allyl acetate, isopropenyl acetate, vinyl propionate, propyl propionate, methyl crotonate, methyl valeate, ethyl butyrate, dibutyl ether, and a mixture thereof; and a mixed solvent consisting of a solvent containing at least one member selected from the group consisting of heptane, dimethyl cyclohexane, ethyl cyclohexane, toluene, ethyl benzene, chlorobenzene, xylene, and a mixture thereof and a solvent containing at least one member selected from the group consisting of diethyl ketone, diisopropyl ketone, methylpropyl ketone, methylisobutyl ketone, methyl-t-butyl ketone, n-propyl acetate, n-butyl acetate, ethyl acrylate, methyl methacrylate, ethyl methacrylate, vinyl acrylate, n-propyl acrylate, allyl acetate, isopropenyl acetate, vinyl propionate, propyl propionate, methyl crotonate, methyl valeate, ethyl butyrate, dibutyl ether, and a mixture thereof may be cited.

As examples of the preferred azeotropic solvent, a solvent containing at least one member selected from the group consisting of heptane, toluene, ethyl benzene, xylene, and mixtures thereof; a mixed solvent consisting of the solvents mentioned above and at least one member selected from the group consisting of ethyl acrylate, methyl methacrylate, ethyl methacrylate, and mixtures thereof or a solvent containing at least one member selected from the group consisting of ethyl methacrylate, diisopropyl ketone, n-propyl acrylate, n-butyl acetate, and a mixture thereof may be cited.

By effecting the azeotropic distillation with the solvent mentioned above, the acrylic acid that is substantially free from the solvent and water can be separated as the bottoms of the distillation column. By the one-column distillation method, acetic acid can be removed at the same time. By the two-column distillation method, the bottoms of the column are further distilled to expel acetic acid.

The amount of the azeotropic solvent to be added is only required to be slightly larger than is required for forming an azeotropic mixture of water and acetic acid (see JP-A-09-157,213).

Method for Separation of High Boiling Impurity

The step of refinement that is targeted at removing a high boiling impurity present in acrylic acid is generally carried out by using a high boiling impurity separation column that is adapted to effect removal of the high boiling impurity from the acrylic acid.

Though a known separation column such as a distillation column is generally used for the separation of a high boiling impurity, a tray column having a theoretical plate number in the range of 1–20 is advantageously used. As regards the operating conditions of the column, the distillation is generally carried out under a reduced pressure, preferably in the range of 10–150 hPa abs at a column bottom temperature in the range of 60–120° C.

The composition of the bottoms obtained in consequence of the refinement effected in the high boiling impurity separation column cannot be generally specified because it is variable with the operating conditions of the respective steps of the process involved. It may comprise 20–65% by weight of acrylic acid, 30–60% by weight of acrylic acid dimer, 5–15% by weight of a polymerization inhibitor (such as hydroquinone), 3–10% by weight of maleic acid, and other high boiling substances, for instance.

The high boiling impurity separation column is preferably provided with a thermal decomposition vessel which is adapted to decompose the bottoms containing high boiling impurities such as acrylic acid dimer and recover acrylic acid consequently. The thermal decomposition vessel used herein is not particularly restricted on account of the form but only required to be capable of decomposing the bottoms containing the aforementioned high boiling impurities and recovering acrylic acid consequently. The temperature of thermal decomposition in the thermal decomposition vessel is generally in the range of 120–220° C. and particularly in the range of 120–160° C. Though the retention time cannot be generally specified because it is variable with the temperature of thermal decomposition, it is generally in the range of 20–50 hours. The thermal decomposition, when carried out at a high temperature for a short period of time, proves unfavorable because these conditions entail adverse phenomena such as polymerization and decomposition.

The treatment for the thermal decomposition is preferably preceded by a pretreatment when the acrylic acid happens to contain impurities such as maleic acid and acrylic acid trimer besides acrylic acid dimer. For example, (1) the acrylic acid solution is distilled in a distillation column to recover acrylic acid through the top of the column and (2) the bottoms of the distillation column are introduced into the thermal decomposition vessel and decomposed therein. This treatment for the thermal decomposition may be directly carried out without being preceded by such a pretreatment when impurities such as maleic acid are present in such a negligibly small amount as to fall below 3% by weight, for example.

The distillation column to be used for the pretreatment is not particularly restricted but only required to be capable of distilling the acrylic acid containing acrylic acid dimer and maleic acid. Since the acrylic acid of this sort has high viscosity, the distillation column to be used is preferably provided with a thin film evaporator. The evaporator, for the purpose of effecting the separation of maleic acid efficiently, is preferably selected with respect to factors such as form and operating conditions, for example. Specifically, the distillation column is preferred to be a tray column that has a theoretical plate number in the range of 1–5, particularly 1–3. As regards the operating conditions, the distillation is carried out advantageously under a reduced pressure, preferably in the range of 10–150 hPa abs at a column bottom temperature of not higher than 120° C., preferably in the range of 60–120° C. If the temperature exceeds 120° C., the excess will render continuous stable operation difficult because of the generation of a precipitate that is considered to originate in maleic acid.

The thin film evaporator is not particularly restricted. Any of the thin film evaporators that are in popular use may be adopted.

At least part of the bottoms which are generated in the thermal decomposition vessel at the step (c) is supplied to the pretreating distillation column of the thermal decomposition vessel or to the step for low boiling impurity separation or to the high boiling separation column so as to recover the acrylic acid contained in the bottoms.

By circulating the waste liquid generated at the step (d), it is possible to preclude polymerization and/or precipitation at the step (c). It is presumed that the compound of the aldehyde treating agent with the aldehyde generated at the step (c) contained in the waste liquid and/or the polymerization inhibitor contained in the bottoms function for some uncertain reasons to preclude the polymerization and the precipitation.

Step (d)

The step of adding an aldehyde treating agent to the crude acrylic acid mentioned above and then subjecting the resultant mixture to vacuum distillation to obtain acrylic acid of high purity.

The term "aldehydes" as used herein refers to those aldehydes that are formed by the reaction mentioned above. As examples of the aldehydes, furfural, acrolein, and benzaldehyde may be cited. The term "acrylic acid of high purity" as used herein refers to the acrylic acid which contains substantially no aldehyde and which fits the production of polymers of acrylic acid such as, for example, an absorbent resin. Generally, the aldehydes are preferred each to account for not more than 10 weight ppm, based on the total weight of the acrylic acid.

The aldehyde treating agent to be used in this invention is not particularly restricted but only required to be a compound which is used for the purpose of removing the aldehyde contained in the acrylic acid-containing liquid and refining the acrylic acid. The function mentioned above may occur in a procedure that comprises binding the liquid with aldehyde and forms a complex and subsequently allows the complex to precipitate and separate itself from acrylic acid or in a procedure that comprises directly effecting decomposition of aldehyde. Thus, the sequence of the mechanism of this function under discussion is irrelevant.

The aldehyde treating agent mentioned above is usable effectively without reference to the discrimination between a liquid state and a gaseous state. It is, however, preferred to be in a liquid state on account of the ease of addition. When the aldehyde treating agent is in a solid state at normal room temperature, therefore, it is preferably dissolved in a proper solvent and used in the form of a solution. The solvent to be used in this case is not particularly restricted but only required to be capable of dissolving the aldehyde treating agent. Preferably, the aldehyde treating agent is dissolved in the same solvent as is contained in the acrylic acid-containing liquid.

The aldehyde treating agents that are usable in this invention include primary amines and/or salts thereof. As examples thereof, amino guanidine, aniline, o-, m-, p-toluidine, o-, m-, p-nitro aniline, glycin, ethanolamine, methylamine, 1,2-diamino ethane, tetramethylene diamine, pentamethylene diamine, hydrazine hydrate, and phenyl hydrazine may be cited. Among other aldehyde treating agents enumerated above, hydrazine hydrate and phenyl hydrazine, which are hydrazine compounds, prove particularly advantageous.

The amount of the aldehyde treating agent to be added to the acrylic acid-containing liquid can be adjusted proportionately to the amount of the aldehyde to be eventually contained therein. In this invention, the aldehyde treating agent is preferably added in an amount in the range of 1.0–10.0 mols, more favorably in the range of 1.0–5.0 mols, per mol of the aldehyde in the acrylic acid-containing liquid.

The crude acrylic acid, after having added the aldehyde treating agent thereto, is refined by vacuum distillation using a known distillation column. This refinement can adopt any of the known refining devices and refining conditions. In a flash column which is furnished with a mist separator, for example, the distillation is effected at a column top pressure in the range of 10–150 hPa abs and a column top temperature in the range of 35–90° C.

For the purpose of setting the relevant parts of the distillation column at the levels of pressure specified above, it is generally preferred to use a vacuum generating device in the form of a steam ejector, a liquid drive type ejector, or a liquid seal type vacuum pump. Further, from the viewpoint of the effective utilization of material, the vacuum generating device is preferred to be so adapted as to employ as a drive source or a sealing liquid such solvent as water which is used at the step (b).

Optionally, a thermal decomposition vessel adapted to recover acrylic acid from the acrylic acid dimer contained in the bottoms of the distillation column at the step (d) may be installed so as to permit return of at least part of the bottoms of the thermal decomposition vessel to the step (c). Here, though at least part of the bottoms of the thermal decomposition vessel at the step (d) could be returned to the step (d), this return is preferably made to the step (c) from the viewpoint of preventing polymerization at the step (c).

Step (e)

The step of returning the waste liquid generated at the preceding step (d) to the step (b) and/or the step (c)

By returning the waste liquid generated at the step (d) to the step (b) or the step (c) or to the step (b) and the step (c), it is possible to recover acrylic acid contained in the waste liquid. As examples of the waste liquid generated at the step (d), the waste liquid generated while the device used at the step (d) is cleaned, the bottoms of the distillation column generated at the step (d), and the waste liquid of the vacuum generating device using at least one member selected from the group consisting of a steam ejector, a liquid drive type ejector, and a liquid seal type vacuum pump at the step (d) may be cited. Particularly, the waste liquid which is generated in the vacuum generating device at the step (d), depending on the concentration of acrylic acid in the waste liquid, is preferably returned as a feed liquid to at least one member selected from the group consisting of part of the absorbing solvent at the step (b), the medium stage of an absorbing device, and the step (c). In the case of the step (c), the destination of the return may be the step of solvent separation, the step of low boiling impurity separation, or the step of high boiling impurity separation, whichever may fit the occasion best. The waste liquid may be returned as part of the absorbing solvent when the concentration of acrylic acid in the waste liquid is not more than 5% by weight or may be supplied to the lower stage of the absorbing device or to the step (c) when the concentration exceeds 30% by weight, for example.

The bottoms of the distillation column contain high boiling substances such as acrylic acid dimer in a large amount. When they are returned as they are to any step, the high boiling substances will simply accumulate in the system and compel the operation of the system to proceed under an overload state. The return of the bottoms to the step of the thermal decomposition of acrylic acid dimer to acrylic acid at the step (c) proves preferable because it permits an increase in the yield of acrylic acid.

Since the conventional process has discarded the bottoms by way of disposal, it has required to decrease the amount of waste liquid even from the economic point of view and heighten the concentration of impurities by a concentration method, for example, and consequently entail problems such as exalting the viscosity of the concentrated liquid and inducing clogging of the piping. In contrast, by returning the waste liquid to a step which precedes the step of its origin, it is possible to secure a fixed flow volume in the piping, keep the concentration of impurities from increasing, and repress the trouble of clogging of the bottoms in the piping system at the step (d). It is presumed that the properties of the waste liquid has no problem.

In the case of producing methacrylic acid, the means or the procedure described above regarding acrylic acid can be utilized as optionally altered or modified with the exception of the following points.

At least one member selected from the group consisting of isobutylene, t-butyl alcohol, methyl-t-butyl ether, methacrolein, and a mixture thereof is subjected to catalytic gas phase oxidation using a molecular oxygen-containing gas. The catalyst to be used for the reaction of oxidation may be any of the known catalysts, which are available for the reaction of interest. In the case of the reaction performed in two stages, a molybdenum-bismuth complex oxide type catalyst is used for the reaction of the first stage and a molybdenum-phosphorus complex oxide type catalyst is used for the reaction of the second stage.

The mixed gas obtained by the reaction is guided to a absorbing column and is absorbed therein as methacrolein and/or methacrylic acid solution and the solution is subsequently distilled and/or stripped by the use of a stripping column so as to eliminate light boiling substances such as methacrolein. The resultant methacrylic acid solution is extracted with a known organic solvent in a known extraction column, the extracted methacrylic acid solution in the solvent is distilled in a distillation column so as to recover or remove the organic solvent, and the crude methacrylic acid consequently obtained is distilled till purification by the use of a known distillation column. The organic solvent to be used herein is an aliphatic saturated hydrocarbon of 6–9 carbon atoms. As examples of the preferred organic solvent, hexane, heptane, octane, and nonane may be cited. For the sake of absorption, stripping, and distillation, any of the known methods of contact may be adopted as in the case of acrylic acid. The crossflow contact using a bubble tray and the counter flow contact using a turbo grid tray may be cited, for example. For the extraction, any of the known methods which are available for the contact of interest, for example, the sequential contact using a tray column fitted with sieve plates and a rotary disc column and the differential contact using a spray column and a packed column may be cited.

EXAMPLES

Now, this invention will be described more specifically below with reference to examples. The following examples are induced merely to aid in the understanding of the invention, and variations may be made by one skilled in the art without departing from the spirit and scope of the invention.

Comparative Example 1

Acrylic acid (1) was obtained by gas phase oxidation of a raw material gas containing propylene and a reaction product containing acrylic acid was absorbed by using water as an absorbing solvent. Consequently, an aqueous acrylic acid solution containing hydroquinone as a polymerization inhibitor was obtained. The aqueous acrylic acid solution had the following composition:

|  |  |
|---|---|
| Acrylic acid | 65% by weight |
| Acetic acid | 3% by weight |
| Maleic acid | 0.5% by weight. |

The aqueous acrylic acid solution containing low boiling impurities and including water was distilled in a sole low boiling impurity separation column (a distillation column using 60 sieve trays) to separate the low boiling substances and water through the top of the column. The bottoms consequently obtained in the column were distilled in a high boiling impurity separation column (distillation column using 35 sieve trays) to separate the high boiling impurities as the bottoms and obtain crude acrylic acid containing aldehydes (2) through the top of the column. This crude acrylic acid and an aqueous 80% by weight hydrazine hydrate solution added thereto as an aldehyde treating agent at a rate of 2 kg/h were together distilled in a flash distillation column with a mist separator operated at an operating pressure of 50 hPa abs to expel acrylic acid of high purity (3) through the top of the column. The bottoms (4) of the distillation column were wholly disposed of by incineration. A steam ejector was used as a device for vacuum generation. The condensate (5) of the ejector was disposed of as a waste liquid. The flow rates of the products of the relevant component reactions were as shown below.

(1) Acrylic acid in the reaction product: 2630 kg/h (2) Crude acrylic acid (acrylic acid: 99.85% by weight): 2550 kg/h (3) Acrylic acid of high purity (acrylic acid: 99.9% by weight): 2500 kg/h (4) Bottoms of acrylic acid of high purity (acrylic acid: 42% by weight): 17 kg/h (5) Ejector condensate of acrylic acid of high purity (acrylic acid: 11% by weight): 300 kg/h.

The yield of acrylic acid of high purity relative to the acrylic acid formed by the reaction was 95.0%. The yield was calculated in accordance with the following formula:

$$\text{Yield}(\%) = (A \times B)/C$$

wherein

A stands for the amount of acrylic acid of high purity (kg/h),

B for the concentration of acrylic acid in the acrylic acid of high purity (% by weight), and C for the amount of acrylic acid in the reaction product (kg/h).

The total amount of the polymer at the step of high boiling impurity separation after six months' continued operation was about 18 kg. In about fourth months of the operation, the pipe for transferring the bottoms to the device for disposition by incineration was clogged and it had be furnished with a bypass to continue the transfer.

Example 1

A crude acrylic acid was obtained and acrylic acid of high purity was produced therefrom by following the procedure of Comparative Example 1. In this case, the bottoms of the column used for the production of the acrylic acid of high purity were wholly returned to an acrylic acid dimer decomposition vessel at the step of high boiling impurity separation and the condensate of ejector was wholly returned to the step of acrylic acid absorption. The flow rates of the products of the relevant component reactions were as follows:

Acrylic acid in the reaction product: 2630 kg/h

Crude acrylic acid (acrylic acid: 99.85% by weight): 3370 kg/h

Acrylic acid of high purity (acrylic acid: 99.9% by weight): 2550 kg/h

Bottoms of acrylic acid of high purity (acrylic acid: 98.5% by weight): 830 kg/h Ejector condensate of acrylic acid of high purity (acrylic acid: 11% by weight): 300 kg/h.

The yield of the acrylic acid of high purity relative to the acrylic acid formed by the reaction was 96.9%. The yield was calculated in accordance with the same formula as in Comparative Example 1. The total amount of the polymer at the step of high boiling impurity separation after six months' continued operation was about 2 kg. The piping system for the bottoms showed no sign of abnormality.

The entire disclosure of Japanese Patent Application No. 2000-26149 filed on Feb. 3, 2000 including specification, claims and summary are incorporated herein by reference in its entirety.

What is claimed is:

1. A method for producing (meth)acrylic acid, which comprising:

(a) a step of obtaining a gaseous reaction product containing (meth)acrylic acid by subjecting at least one member selected from the group consisting of propylene, propane, acrolein, and a mixture thereof or at least one member selected from the group consisting of isobutylene, t-butyl alcohol, methyl-t-butyl ether, methacrolein, and a mixture thereof to the reaction of catalytic gas phase oxidation;

(b) a step of absorbing the gaseous reaction product by the use of a solvent;

(c) a step of separating said solvent, a low boiling impurity, and a high boiling impurity from the (meth) acrylic acid solution absorbed with said solvent by extraction and/or distillation and obtaining crude (meth)acrylic acid solution containing aldehydes having boiling points approximating closely to the boiling point of (meth) acrylic acid as impurities;

(d) a step of adding an aldehyde treating agent to said crude (meth)acrylic acid and subjecting the resultant mixture to vacuum distillation thereby obtaining (meth) acrylic acid of high purity; and (e) a step of returning the waste liquid generated in said step (d) to said step (b) and/or said step (c).

2. A method according to claim 1, wherein the solvent in the step (b) is at least one member selected from the group consisting of water, diphenyl ether, diphenyl, a mixture of diphenyl and diphenyl ether, water, acrylic acid, a mixture of acrylic acid with water, acetic acid and a mixture of acetic acid with water.

3. A method according to claim 1, wherein in the step (c), the extraction is a solvent extraction method, and the distillation is a distillation by the use of an azeotropic solvent.

4. A method according to claim 3, wherein the azeotropic solvent is a first solvent containing at least one member selected from the group consisting of heptane, dimethyl cyclohexane, ethyl cyclohexane, toluene, ethyl benzene, chlorobenzene, xylene, and a mixture thereof.

5. A method according to claim 3, wherein the azeotropic solvent is a second solvent containing at least one member selected from the group consisting of diethyl ketone, diisopropyl ketone, methylpropyl ketone, methylisobutyl ketone, methyl-t-butyl ketone, n-propyl acetate, n-butyl acetate, ethyl acrylate, methyl methacrylate, ethyl methacrylate, vinyl acrylate, n-propyl acrylate, allyl acetate, isopropenyl acetate, vinyl propionate, propyl propionate, methyl crotonate, methyl valeate, ethyl butyrate, dibutyl ether, and a mixture thereof.

6. A method according to claim 3, wherein the azeotropic solvent is a mixed solvent consisting of the first solvent containing at least one member selected from the group consisting of heptane, dimethyl cyclohexane, ethyl cyclohexane, toluene, ethyl benzene, chlorobenzene, xylene, and mixtures thereof and the second solvent containing at least one member selected from the group consisting of diethyl ketone, diisopropyl ketone, methylpropyl ketone, methylisobutyl ketone, methyl-t-butyl ketone, n-propyl acetate, n-butyl acetate, ethyl acrylate, methyl methacrylate, ethyl methacrylate, vinyl acrylate, n-propyl acrylate, allyl acetate, isopropenyl acetate, vinyl propionate, propyl propionate, methyl crotonate, methyl valeate, ethyl butyrate, dibutyl ether, and a mixture thereof.

7. A method according to claim 4, wherein the first solvent is at least one member selected from the group consisting of heptane, toluene, ethyl benzene, xylene, and a mixture thereof.

8. A method according to claim 5, wherein the second solvent is at least one member selected from the group consisting of ethyl methacrylate, diethyl ketone, methylpropyl ketone, methylisobutyl ketone, methyl-t-butyl ketone, n-butyl acetate, and a mixture thereof.

9. A method according to claim 6, wherein the mixed solvent is a mixture of at least one member selected from the group consisting of heptane, toluene, ethyl benzene, xylene, and a mixture thereof with at least one member selected from the group consisting of ethyl methacrylate, diethyl ketone, methylpropyl ketone, methylisobutyl ketone, methyl-t-butyl ketone, n-butyl acetate, and a mixture thereof.

10. A method according to claim 1, wherein in the step (c), the high boiling impurity is further separated by the use of a distillation column with a theoretical plate of 1 to 20.

11. A method according to claim 1, wherein the waste liquid generated at said step (d) is the bottoms of a column for distillation at said step (d).

12. A method according to claim 1, wherein said step (c) and/or said step (d) is furnished with a thermal decomposition vessel for recovering (meth)acrylic acid from (meth)acrylic acid dimer.

13. A method according to claim 1, wherein the waste liquid generated at said step (d) is the waste liquid in a vacuum generating device operated at said step by using at least one member selected from the group consisting of a steam ejector, a liquid drive ejector, and a liquid seal vacuum pump.

14. A method according to claim 1, wherein the waste liquid generated in a device for vacuum generation at said step (d), depending on the concentration of (meth)acrylic acid in said waste liquid, is returned as a feed liquid to at least one member selected from the group consisting of part of the absorbing solvent at said step (b), the medium stage of an absorbing device, and said step (c).

15. A method according to claim 1, wherein the waste liquid generated while a device used at said step (d) is cleaned is returned to said step (b) and/or said step (c).

16. A method according to claim 1, wherein said aldehyde treating agent is a primary amine and/or a salt thereof.

17. A method according to claim 16, wherein said aldehyde treating agent is at least one member selected from the group consisting of amino guanidine, aniline, o-, m-, p-toluidine, o-, m-, p-nitro aniline, glycin, ethanol amine, methyl amine, 1,2-diamino ethane, tetramethylene diamine, pentamethylene diamine, hydrazine hydrate, and phenyl hydrazine.

18. A method according to claim 17, wherein said aldehyde treating agent is at least one member selected from the group consisting of hydrazine hydrate and phenyl hydrazine.

19. A method according to claim 17, wherein said aldehyde treating agent accounts in the range of 1.0 to 10.0 mols, per mol of the aldehyde in the acrylic acid-containing liquid.

20. A method according to claim 19, wherein said aldehyde treating agent accounts in the range of 1.0 to 5.0 mols, per mol of the aldehyde in the acrylic acid-containing liquid.

* * * * *